United States Patent [19]
Johnson et al.

[11] Patent Number: 5,476,835
[45] Date of Patent: Dec. 19, 1995

[54] HERBICIDAL IMIDAZOLINONE EXTRUDED GRANULAR COMPOSITIONS

[75] Inventors: Jerry L. Johnson, Lawrenceville, N.J.; Joseph Kimler, Yardville, N.Y.

[73] Assignee: American Cyanamid Company, Wayne, N.J.

[21] Appl. No.: 270,983

[22] Filed: Jul. 5, 1994

Related U.S. Application Data

[63] Continuation of Ser. No. 54,764, Apr. 28, 1993, abandoned.

[51] Int. Cl.$^6$ ..................... A01N 43/50
[52] U.S. Cl. .............. 504/247; 504/253; 504/277
[58] Field of Search ............... 504/247, 253, 504/277

[56] References Cited

U.S. PATENT DOCUMENTS

| | | | |
|---|---|---|---|
| 4,188,487 | 2/1980 | Los | 504/277 |
| 4,772,311 | 9/1988 | Los | 504/246 |
| 4,798,619 | 1/1989 | Los | 504/246 |
| 5,039,333 | 8/1991 | Finn | 71/92 |
| 5,108,485 | 4/1992 | Doehner, Jr. | 71/92 |
| 5,180,415 | 1/1993 | Omid | 504/299 |
| 5,180,587 | 1/1993 | Moore | |

FOREIGN PATENT DOCUMENTS

| | | |
|---|---|---|
| 0182120 | 5/1986 | European Pat. Off. |
| 0252897 | 1/1988 | European Pat. Off. |
| 254951 | 2/1988 | European Pat. Off. |
| 322616 | 7/1989 | European Pat. Off. |
| 447056 | 9/1991 | European Pat. Off. |
| 2215171 | 8/1974 | France. |
| WO89/00079 | 1/1989 | WIPO. |

OTHER PUBLICATIONS

Chemical Patents Index, Documentation Abstracts Journal, Section Ch, Week 9131, 2 Oct. 1991 Derwent Publications Ltd., London, GB; Class C, AN 226813 and JP-A-3 146 126 (Sankyo KK) 21 Jun. 1991.

*Primary Examiner*—S. Mark Clardy
*Attorney, Agent, or Firm*—Gregory M. Hill

[57] ABSTRACT

The present invention relates to a herbicidal extruded granular composition which is solvent free, dust free, and demonstrates improved water dispersibility properties. Said herbicidal composition also has improved environmental compatibility.

10 Claims, No Drawings

HERBICIDAL IMIDAZOLINONE EXTRUDED GRANULAR COMPOSITIONS

This is a continuation of application(s) Ser. No. 08/054,764 filed on Apr. 28, 1993, now abandoned.

BACKGROUND OF THE INVENTION

Herbicides are commonly formulated as wettable powders, dispersible granules, emulsifiable concentrates, aqueous flowables and the like. Of these, the dispersible granular formulations offer ease of handling, for instance spills can be readily swept up, and of course, the absence of an organic, flammable solvent. In general, such formulations offer increased chemical stability over liquid formulations. Further, granular formulations offer the ability to employ higher concentrations of active ingredient, i.e. 70% or greater vs. 15% to 45% for the average liquid formulation and, thereby, significantly reduce the bulk of the final product.

The most widely used method for preparing water dispersible granular compositions is pan granulation. However, the particle size of the final granulated product is difficult to control and can give the final product uneven and undesirable dispersibility properties. Pan granulation is also an inherently dusty process.

An alternative method to formulate a granular composition is by extrusion. Extruded dry granular compositions, however, tend to produce tightly compacted granules which possess poor dispersibility and suspendability.

Therefore, it is an object of this invention to provide a herbicidal extruded granular composition with no dust and improved water dispersibility and suspendability.

It is a further object of this invention to provide an herbicidal extruded granular composition having granules of substantially uniform size and density.

It is also an object of this invention to provide a herbicidal extruded granular composition requiring less surfactant than the corresponding pan granulated product.

It is a further object invention to provide a herbicidal extruded granular composition that is solvent-free and able to be packaged in a water soluble container, resulting in increased environmental compatibility and user safety.

SUMMARY OF THE INVENTION

The present invention relates to a herbicidal extruded granular composition comprising an active ingredient, such as an imidazolinone herbicide, an inert carrier, a wetting agent, and a dispersing agent. Said compositions are dust free, storage stable, readily dispersible, and environmentally compatible.

DESCRIPTION OF THE INVENTION

The imidazolinone class of herbicides such as imazaguin, imazethapyr, imazamethapyr and imazamethabenz are highly sought after for the selective control of a wide breadth of grass and broadleaf weeds in the presence of agricultural crops at exceptionally low rates of application. At present, imidazolinone herbicides are commercially available mainly in the form of liquid compositions. However, as environmental concerns increase, there is an ever-growing need for an effective dry composition containing an imidazolinone herbicide. The prior art,s pan granulated compositions present certain drawbacks such as dusting, variable particle size distribution, and lack of ease of water dispersibility. Moreover, extruded granular compositions can produce tightly compacted granules which are difficult to suspend and resuspend in water. Efforts to overcome the drawbacks of extruded herbicidal granular compositions have recently been described in commonly assigned, copending patent applications, Ser. Nos. 07/996,412 and 07/996,221, filed concurrently on Dec. 23, 1992.

It has now been found that extrudable granulated herbicidal compositions comprising an imidazolinone herbicide, an inert carrier, a wetting agent and a dispersing agent can be formulated to possess improved suspendability and dispersibility. The imidazolinone herbicide may be any of the imidazolinone compounds known in the art such as those described in U.S. Pat. Nos. 4,798,619; 4,772,311; 5,039,333; 5,108,485; and in EP 254,951 and EP 322,616. Preferably the imidazolinone herbicide is selected from imazaguin, imazapyr, imazethapyr and imazamethapyr. A more preferred imidazolinone herbicide is imazaguin. In the compositions of the invention the imidazolinone herbicide may be present in the amount, on a weight to weight basis, of about 50% to 90%, preferably about 60% to 80%, more preferably about 70% to 75%.

The inert carrier component of the compositions of the invention is present at about 2% to 40% (w/w), preferably about 5% to 30%, more preferably 15% to 25%. Inert carriers suitable for use in the compositions of the invention are those materials well known in the art such as kaolin clay, talc, montmorillonite, bentonite, attapulgite, diatomaceous earth and the like, preferably kaolin clay. The inert carrier is present in the inventive composition in an amount sufficient to produce, on a weight to weight basis, a composition with an ingredient total of 100%. In general, this would be an amount of about 2% to 40%, preferably 5% to 30%, more preferably about 15% to 25% by weight. It is understood that the amount of inert carrier is proportioned to the purity of the active ingredient used, i.e. the less pure the active ingredient (75% technical grade), the less inert carrier is added and the more pure the active ingredient (95% technical grade), the more inert carrier is added.

About 3% to 8% by weight, preferably about 4% to 7%, more preferably about 6.5% to 7.5%, and most preferably about 7% of a mixture comprising about 1 part dispersing agent and 2 parts wetting agent, preferably about I part to 1.8 parts, has been discovered to produce a composition having consistently uniform particle size, and improved water dispersibility and suspendability. Suitable wetting agents for use in the composition of the invention are any of the conventional agents known in the art. Preferable wetting agents are anionic agents such as sodium N-methyl-N-oleyoyltaurate, octylphenoxy polyethoxy ethanol, nonylphenoxy polyethoxy ethanol, sodium dioctyl sulfosuccinate, sodium dodecyl benzyl sulfonate, sodium lauryl sulfonate, sodium alkyl naphthalene sulfonate, sodium sulfonated alkyl carboxylate, and the like or mixtures thereof. Most preferable is a mixture of sodium alkyl naphthalene sulfonate and sodium alkyl carboxylate.

Similarly, dispersing agents useful in the inventive compositions are conventional agents well known in the art, preferably anionic agents such as sodium lignosulfonate, sodium naphthalene formaldehyde condensate, and the like or mixtures thereof, more preferably sodium naphthalene formaldehyde condensate.

Advantageously, it has been found that when the ratio of wetting agent to dispersing agent is about 1.0:2.0, preferably about 1.0:1.8, and the total weight % of the wetting agent/dispersing agent component is about 3% to 8%, preferably about 4% to 7%, more preferably about 6.5% to 7.5%, and most preferably about 7%, an extrudable composition with superior water dispersibility properties and reduced total weight % surfactant is obtained.

The composition of the invention can be prepared by admixing the imidazolinone herbicide, the inert carrier, the wetting agent and dispersing agent in a blender, milling the blended mixture, placing the milled material into a kneader, adding about 10–20% water and kneading mechanically to obtain an extrudable mixture. The extrudable mixture is then passed through an extruder, dried, broken and screened to obtain the desired herbicidal extruded granular composition.

For a more clear understanding of the invention specific examples thereof are set forth below. These examples are merely illustrative and are not to be understood as limiting the scope of the invention in any way.

EXAMPLE 1

Preparation of herbicidal extruded granular compositions

The imidazolinone herbicide, imazaquin, used is the 95% technical material. The inert carrier used is Kaolin clay. The wetting agent used is a proprietary blend of sodium alkyl naphthalene sulfonate and sodium sulfonated alkyl carboxylate, MORWET® EFW, manufactured by Witco Incorporated, Houston, Tex. The dispersing agent used is sodium naphthalene formaldehyde, condensate, MORWET® D-425, also manufactured by Witco Incorporated. All the ingredients are blended mechanically until homogeneous. The blended mixture is milled using an air-classifying mill. The milled material is introduced into a kneader, 15% wt/wt water is added and the resultant mixture is mechanically kneaded to obtain an extrudable material. This material is extruded using a bench top basket extruder, for example, the extruder manufactured by LCI Incorporated, Charlotte, N.C.. The extruded material is dried and broken in a fluid bed and screened to obtain the desired particle size.

Using the above procedure, the compositions shown in Table I are prepared.

undisturbed for 30 minutes. A 25 mL sample is then removed from the center of the cylinder and dried to constant weight. The suspendability is reported as a % of the ideal theoretical value.

Resuspendability

One gram of test composition is placed in a 100 mL cylinder containing 100 mL standard hard water. The cylinder is stoppered, inverted 30 times and allowed to stand undisturbed for 24 hours. After 24 hours, the cylinder is reinverted until the solid is evenly resuspended. The number of inversions required to resuspend the solid is recorded.

Each evaluation is duplicated for all the test compositions. The results are shown on Table II.

TABLE II

Evaluation of Test Compositions

| Composition | Ratio WA:DA* | WA + DA* (wt/wt %) | Dispersibility (Inversions) | Suspendability (%) | Resuspendability (Inversions) |
|---|---|---|---|---|---|
| A | 1:3 | 4 | 5 | 74.1 | 2 |
| B | 3.5:1 | 10 | 10 | 124.2 | 4 |
| C | 4.3:1 | 16 | 11 | 119.5 | 10 |
| D | 1:1.3 | 16 | 10 | 116.9 | 19 |
| E | 1:15 | 16 | 11 | 117.2 | 17 |
| F | 1:9 | 10 | 13 | 113.4 | 2 |
| G | 1:1.8 | 7 | 6 | 95.7 | 2 |
| H | 1.2:1 | 13 | 10 | 122.6 | 10 |
| I | 1:2.25 | 13 | 14 | 124.8 | 15 |
| J | 1:1.5 | 10 | 14 | 119.0 | 2 |

*WA designates Wetting Agent and DA designates Dispersing Agent

What is claimed is:

1. A water-dispersible herbicidal extruded granular composition consisting essentially of about 50% to 90% by weight of an imidazolinone herbicide, an inert carrier, and about 3% to 8% by weight of a mixture of a wetting agent selected from the group consisting of N-methyl-N-oleyoyltaurate, octylphenoxy polyethoxy ethanol, nonylphenoxy

TABLE I

Extruded Granular Compositions

| Ingredient | % Weight/Weight | | | | | | | | | |
|---|---|---|---|---|---|---|---|---|---|---|
|  | A | B | C | D | E | F | G | H | I | J |
| Imazaquin (95% tech.) | 77.1 | 77.1 | 77.1 | 77.1 | 77.1 | 77.1 | 77.1 | 77.1 | 77.1 | 77.1 |
| Wetting agent | 1.0 | 7.0 | 13.0 | 7.0 | 1.0 | 1.0 | 2.5 | 7.0 | 4.0 | 4.0 |
| Dispersing agent | 3.0 | 3.0 | 3.0 | 9.0 | 15.0 | 9.0 | 4.5 | 6.0 | 9.0 | 6.0 |
| Kaolin clay | 18.9 | 12.9 | 6.9 | 6.9 | 6.9 | 12.9 | 15.9 | 9.9 | 9.9 | 12.9 |
|  | 100.0 | 100.0 | 100.0 | 100.0 | 100.0 | 100.0 | 100.0 | 100.0 | 100.0 | 100.0 |

EXAMPLE 2

Evaluation of the dispersibility, suspendability and resuspendability of test compositions Dispersibility One gram of the test composition is placed in a 100 mL cylinder containing 100 mL of standard hard water (342 ppm calcium and magnesium ion content). The cylinder is stoppered and inverted 360° until the solid is evenly dispersed. The number of 360° inversions required to disperse the solid is recorded.

Suspendability

One gram of test composition is placed in a 250 mL cylinder containing 250 mL standard hard water. The cylinder is stoppered, inverted 30 times and allowed to stand polyethoxy ethanol, sodium dioctyl sulfosuccinate, sodium dodecyl benzyl sulfonate, sodium lauryl sulfonate, sodium alkyl naphthalene sulfonate, sodium sulfonated alkyl carboxylate, and mixtures thereof, and sodium naphthalene formaldehyde condensate as a dispersing agent present in the ratio of about 1 part wetting agent to 2 parts dispersing agent.

2. The composition according to claim 1 wherein the ratio of the wetting agent to dispersing agent is about i part wetting agent to 1.8 parts dispersing agent.

3. The composition according to claim 1 wherein the mixture of wetting agent and dispersing agent is present in the amount of about 4% to 7% by weight.

4. The composition according to claim 3 wherein the mixture of wetting agent and dispersing agent is present in the amount of about 7% by weight.

5. The composition according to claim 1 the imidazolinone herbicide is present in the amount of about 60% to 80% by weight.

6. The composition according to claim 5 wherein the imidazolinone herbicide is present in the amount of about 70% to 75% by weight.

7. The composition according to claim 1 wherein the imidazolinone herbicide is selected from the group consisting of imazaquin, imazapyr, imazethapyr and imazamethapyr.

8. The composition according to claim 7 wherein the imidazolinone herbicide is imazaguin.

9. The composition according to claim 5 wherein the imidazolinone herbicide is imazaguin and the mixture of wetting agent and dispersing agent is present in the amount of about 7%.

10. The composition according to claim 9 wherein the wetting agent and dispersing agent are present in a ratio of about i part wetting agent to about 1.8 parts dispersing agent.

* * * * *